United States Patent [19]

Elslager et al.

[11] Patent Number: 4,853,221

[45] Date of Patent: Aug. 1, 1989

[54] METHOD FOR TREATING NON-SMALL CELL LUNG CANCER, HEAD AND NECK CANCERS AND BREAST CANCER

[75] Inventors: Edward F. Elslager; Wilbur R. Leopold, III, both of Ann Arbor, Mich.

[73] Assignee: Warner-Lambert Company, Morris Plains, N.J.

[21] Appl. No.: 112,919

[22] Filed: Oct. 23, 1987

Related U.S. Application Data

[60] Continuation-in-part of Ser. No. 15,597, Feb. 17, 1987, abandoned, which is a continuation of Ser. No. 820,779, Jan. 21, 1986, abandoned, which is a continuation-in-part of Ser. No. 691,614, Jan. 15, 1985, abandoned, which is a continuation of Ser. No. 471,681, Dec. 20, 1982, abandoned, which is a division of Ser. No. 206,596, Nov. 13, 1980, Pat. No. 4,391,809, which is a continuation of Ser. No. 84,944, Oct. 15, 1979, abandoned.

[51] Int. Cl.[4] .................. A61K 31/66; A61K 31/44; A61K 33/24; A61K 31/70; A61K 31/505; A61K 31/52

[52] U.S. Cl. ...................... 424/649; 514/34; 514/262; 514/260; 514/110; 514/281; 514/274

[58] Field of Search ............... 514/34, 274, 260, 110, 514/262, 281; 424/131

[56] References Cited

U.S. PATENT DOCUMENTS

4,376,858  3/1983  Colbry ........................... 544/291
4,391,809  7/1983  Elslager ......................... 424/251

FOREIGN PATENT DOCUMENTS

1345502  1/1974  United Kingdom .

*Primary Examiner*—Jerome D. Goldberg
*Attorney, Agent, or Firm*—Ronald A. Daignault

[57] ABSTRACT

5-Methyl-6-[[(3,4,5-trimethoxyphenyl)amino]-methyl]-2,4-quinazolinediamine (trimetrexate) has been shown to possess clinical activity against non-small cell lung cancer, head and neck squamous cancers, and breast cancer. The compound also demonstrates therapeutic synergy with several known antineoplastic agents. Methods of treating non-small cell lung cancer, head and neck cancers, and breast cancer by administering trimetrexate alone or in combination with other neoplastic agents is disclosed.

16 Claims, No Drawings

METHOD FOR TREATING NON-SMALL CELL LUNG CANCER, HEAD AND NECK CANCERS AND BREAST CANCER

CROSS-REFERENCE TO RELATED APPLICATIONS

This application is a continuation-in-part of copending application Ser. No. 015,597 filed Feb. 17, 1987 now abandoned, which is a continuation of application Ser. No. 820,779 filed Jan. 21, 1986 (now abandoned), which is a continuation-in-part of application Ser. No. 691,614 filed Jan. 15, 1985 (now abandoned), which is a continuation of application Ser. No. 471,681 filed Dec. 20, 1982 (now abandoned), which is a divisional of application Ser. No. 206,596 filed Nov. 13, 1980 (now U.S. Pat. No. 4,391,809), which is a continuation of application Ser. No. 084,944 filed Oct. 15, 1979 (now abandoned).

BACKGROUND OF THE INVENTION

The present invention relates to medical methods of treatment. More particularly, this invention concerns methods of treating non-small cell lung cancer, head and neck cancers, and breast cancers in mammals, including man, employing 5-methyl-6-[[(3,4,5-trimethoxyphenyl)amino]methyl]-2,4-quinazolinediamine or a pharmaceutically acceptable salt thereof alone or in combination with other antineoplastic agents.

Antifolate drugs have been used in cancer chemotherapy for over thirty years. N-[4-[[(2,4-diamino-6-pteridinyl)methyl methylamino]benzoyl]-L-glutamic acid, also commonly known as methotrexate, is an antifolate drug which has been used in the treatment of gestational choriocarcinoma and in the treatment of patients with chorioadenoma destruens and hydatiform mole. It is also useful in the treatment of advanced stages of malignant lymphoma, and in the treatment of advanced cases of mycosis fungoides.

However, many patients with cancers of the head and neck, choriocarcinoma, certain forms of lung cancer, and others, do not respond to methotrexate, and patients who do respond initially often relapse. Also, many patients with other forms of cancer such as common gastrointestinal malignancies, rarely respond to methotrexate chemotherapy.

Research efforts have therefore focused on the discovery of new antifolate compounds which have a broader spectrum of antineoplastic activity, which overcome the common mechanism of methotrexate resistance, and which have a more acceptable toxicity profile.

SUMMARY AND DETAILED DESCRIPTION

The present invention provides a method of treating non-small cell lung cancer, head and neck squamous cancers, and breast cancers in mammals in need of such treatment, including man, comprising administering an antineoplastically effective amount of 5-methyl-6-[[(3,4,5-trimethoxyphenyl)amino]methyl]-2,4-quinazolinediamine or a pharmaceutically acceptable salt thereof either alone or in combination with an antineoplastically effective amount of a compound selected from the group consisting of (8S,10S)-10-(3-amino-2,3,6-trideoxy-α-L-lyxo-hexopyranosyl)oxy]-8-glycoloyl-7,8,9,10-tetrahydro-6,8,11-trihydroxy-1-methoxy-5,12-naphthacenedione or a pharmaceutically acceptable salt thereof; 5-fluoro-2,4(1H,3H) -pyrimidinedione or a pharmaceutically acceptable salt thereof; 2-amino-1,7-dihydro-6H-purine-6-thione or a pharmaceutically acceptable salt thereof; 22-oxo-vincaleukoblastine or a pharmaceutically acceptable salt thereof; 2-bis[(2-chloroethyl)amino]tetrahydro-2H-1,3,2-oxazaphosphorine, 2-oxide, or a pharmaceutically acceptable salt thereof; N-[4-[[(2,4-diamino-6pteridinyl)methyl]methylamino]benzoyl]-L-glutamic acid, or a pharmaceutically acceptable salt thereof; or cis-diamminedichloroplatinum (II).

5-Methyl-6-[[(3,4,5-trimethoxyphenyl)amino]methyl]-2,4-quinazolinediamine is commonly known as trimetrexate. It is a potent inhibitor of the enzyme dihydrofolate reductase isolated from a variety of eukaryotic species, including protozoans and mammalian cells and is thus a potent antifolate drug. Trimetrexate reaches a higher concentration than methotrexate in cells in culture, and is more potent than methotrexate in inhibiting the growth of cancer cells in culture. Trimetrexate has shown activity against a variety of transplanted rodent tumors which are resistant to methotrexate and clinical studies in humans have shown trimetrexate to be active against non-small cell lung cancer, head and neck squamous cancers, and breast cancer.

In addition, trimetrexate has been shown to exhibit therapeutic synergism with several known clinically active antineoplastic agents in tests against transplanted P388 murine tumors.

(8S,10S)-10-[(3-Amino-2,3,6-trideoxy-α-L-lyxo-hexopyranosyl)oxy]-8-glycoloyl-7,8,9,10-tetrahydro-6,8,11-trihydroxy-1-methoxy-5,12-naphthacenedione, more commonly known as doxorubicin, is a cytotoxic anthracycline antibiotic isolated from cultures of *Streptomyces peucetius* var. *caesius*.

Doxorubicin has been used successfully to produce regression in disseminated neoplastic conditions such as acute lymphoblastic leukemia, acute myeloblastic leukemia, Wilm's tumor, neuroblastoma, soft tissue and bone sarcomas, breast carcinoma, ovarian carcinoma, transitional cell bladder carcinoma, thyroid carcinoma, lymphomas of both Hodgkin and non-Hodgkin types, bronchogenic carcinoma, and gastric carcinoma.

5-Fluoro-2,4(1H,3H)-pyrimidinedione, also commonly known as 5-fluorouracil, is an antimetabolite which is effective in the palliative management of carcinoma of the colon, rectum, breast, stomach, and pancreas in patients who are considered incurable by surgical or other means.

2-Amino-1,7-dihydro-6H-purine-6-thione, also commonly known as 6-thioguanine, is effective in the therapy of acute non-pymphocytic leukemias.

22-Oxo-vincaleukoblastine, also commonly known as vincristine, is an alkaloid obtained from the common periwinkle plant (*Vinca rosea,* Linn.) and is useful in the treatment of acute leukemia. It has also been shown to be useful in combination with other ocolytic agents in the treatment of Hodgkin's disease, lymphosarcoma, reticulum-cell sarcoma, rhabdomyosarcoma, neuroblastoma, and Wilm's tumor.

2-bis[(2-Chloroethyl)amino]tetrahydro-2H-1,3,2-oxazaphosphorine, 2-oxide, also commonly known as cyclophosphamide, is used in the treatment of Stages III and IV malignant lymphomas, multiple myeloma, leukemia, mycosis fungoides, neuroblastoma, ovarian adenocarcinoma, retinoblastoma, and carcinoma of the breast.

cis-Diamminedichloroplatinum (II), also commonly known as cisplatin, is useful in the palliative treatment of metastatic testicular and ovarian tumors, and for the treatment of transitional cell bladder cancer which is not amenable to surgery or radiotherapy.

In-vitro Preclinical Cell Culture Studies with Trimetrexate

Two leukemia cell lines (L1210 and L5178Y) and two solid tumor cell lines (Sarcoma 180 and Walker 256) were used in these studies.

Logarithmically growing L1210 cells (approximately $3 \times 10^5$ cells/ml) were diluted with Fischer's medium (containing 10% horse serum) to an approximate concentration of $5 \times 10^4$ cells/ml. Cells were planted in duplicate into 15 ml culture tubes containing either no drug or various amounts of drug, and incubated for 48 hours at 37° C. before being counted. As shown by the data appearing in Table I, the results of these tissue culture studies with 5-methyl-6-[[(3,4,5-trimethoxyphenyl)amino]methyl]-2,4-quinazolinediamine (trimetrexate) demonstrate that the compound is a potent inhibitor of L1210 cell growth. The data in Table I also show trimetrexate to be a more potent inhibitor of L1210 cell growth than N-[4-[[(2,4-diamino-6-pteridinyl)methyl]methylamino]benzoyl]-L-glutamic acid (methotrexate).

Trimetrexate was also evaluated in a similar manner side-by-side with methotrexate for its effect on the growth of three additional murine cell lines (L5178Y, Sarcoma-180, and Walkler-256) and three human cell lines (acute myelogenous leukemia K-562, T-cell 8402, and B-cell 8392), propagated in vitro.

The results appear in Table II and demonstrate that trimetrexate was more potent than methotrexate against all of the murine tumor cell lines tested, although against L5178Y it appeared to be only slightly more effective on a molar basis. As against the human cell lines, trimetrexate was more effective in inhibiting cell growth in vitro than was methotrexate.

TABLE I

Comparison of the Inhibition of Cell Growth of L1210 Cells In Vitro by Trimetrexate and Methotrexate

| Compound | $ED_{50}$* for L1210 Cells |
|---|---|
| Trimetrexate | $0.7 \times 10^{-8}$ M |
| Methoxtrexate | $0.8 \times 10^{-8}$ M |

*$ED_{50}$ = the concentration of drug required to reduce the cell count to 50%, determined by plotting the cell count versus drug concentration.

TABLE II

Comparison of the Inhibitory Activity of Trimetrexate and Methotrexate Against Three Murine Tumor Cell Lines and Three Human Tumor Cell Lines Grown In Vitro

| Cell Line | $ED_{50}$ Trimetrexate | $ED_{50}$ Methotrexate |
|---|---|---|
| Murine L5178Y | $0.2 \times 10^{-8}$ M | $0.3 \times 10^{-8}$ M |
| Murine Sarcoma-180 | $1.8 \times 10^{-8}$ M | $4.2 \times 10^{-8}$ M |
| Murine Walker-256 | $0.5 \times 10^{-8}$ M | $0.9 \times 10^{-8}$ M |
| Human AML K-562 | $1.0 \times 10^{-8}$ M | $5.0 \times 10^{-8}$ M |
| Human T-Cell 8402 | $1.0 \times 10^{-8}$ M | $2.5 \times 10^{-8}$ M |
| Human B-Cell 8392 | $0.5 \times 10^{-8}$ M | $2.5 \times 10^{-8}$ M |

The activity of trimetrexate was compared with that of methotrexate in tests with a human tumor cloning system (Latham, et al., *Proc. Am. Assoc. Cancer Res.*, 24: 278 (1983)). The data from these tests appear in Table III were the activities are expressed as the numbers of tumors with 50% or greater reduction in tumor colony forming units after one hour exposure to the drug.

TABLE III

Comparison of Trimetrexate with Methotrexate Activity in a Human Tumor Cloning System

| Tumor | Number of Tumor Specimens | Number of Tumors with 50% or Greater Decrease in Tumor Colony Forming Units | | |
|---|---|---|---|---|
| | | Trimetrexate | | Methotrexate |
| | | 0.1 μg/ml | 1.0 μg/ml | 0.3 μg/ml |
| Breast | 10 | 0 | 2 | 1 |
| Colon | 9 | 4 | 4 | 2 |
| Lung | 8 | 1 | 1 | 1 |
| Melanoma | 5 | 2 | 3 | 1 |
| Ovarian | 6 | 1 | 1 | 0 |
| Renal | 6 | 1 | 1 | 1 |
| Miscell. | 10 | 2 | 1 | 1 |
| Totals | 54 | 11 | 13 | 7 |

Comparing the data for trimetrexate and methotrexate appearing in Table III, 15% (8/54) of the human tumor cultures employed in this assay were sensitive to trimetrexate at a concentration of 0.1 μg/ml and resistance to methotrexate at a concentration of 0.3 μg/ml. On the other hand, only 7% (4/54) were sensitive to methotrexate and resistant to trimetrexate. These data indicate that the mechanisms of uptake or cytotoxicity of the two drugs are dissimilar and that trimetrexate may be useful in tumor types which are resistant to methotrexate.

In Vivo Preclinical Studies with Trimetrexate

The growth inhibition properties of 5-methyl-6-[[(3,4,5-trimethoxyphenyl)amino]methyl]-2,4-quinazolinediamine (trimetrexate) against several transplanted murine tumors were evaluated employing the antitumor screening program of the Drug Evaluation Branch of the National Cancer Institute. The protocols for these tests is described in *Cancer Chemotherapy Reports*, 3: 1–103 (1972). The dosing schedules are results from these tests appear in Table IV.

In the L1210, P388, and B-16 melanoma models, results are expressed as a percentage of median control survival time. Percentage of increase in survival time and/or cures (30 day survivors) were the parameters used to measure the effectiveness of the agents. An initial median survival value for treated over control percentage (% T/C) equal to or greater than 125% was considered indicative of activity. For confirmatory activity, two multidose assays must show % T/C values equal to or greater than 150%.

Percent increase in median life span (% ILS) values appearing in the tables were calculated from the formula; 100×(median life span in days of treated mice minus median life span in days of untreated mice) divided by median life span in days of untreated mice. That is, $\% \ ILS = [100 \times (T-C)]/C$. % T/C and %ILS are directly interconvertible by the formula % $ILS = \% \ T/C - 100$.

(a) Tumors

L1210 Leukemic Cells ($10^5$/mouse) and P388 leukemic cells ($10^6$/mouse) were in the ascites form and were transferred to BD2F₁ or CD2F₁ mice by intraperitoneal (ip) injection of 0.1 ml of cells taken from animals bearing 6- to 7-day old tumors. Leukemic cells were injected ip one day prior to the start of treatment.

B16 Melanotic melanoma was implanted into BD2F$_1$ mice in the form of a tumor "brei" prepared from a 1:10 weight/volume homogenate of the tumor in balanced salt solution.

Colon adenocarcinoma Nos. 26 and 38. Colon adenocarcinoma 26 was propagated in Balb/cj mice for 12 to 15 days. After this time, 0.5 ml of a 1% tumor brei, prepared from several excised subcutaneously passaged tumors, was implanted intraperitoneally into CDF$_1$ mice. Animals were treated with drug ip on Days 1 and 5 following tumor implantation. The median survival time of the treated animals was determined and expressed as a percentage of the median survival time of untreated control animals.

Colon adenocarcinoma 38 was propagated in C57BL/6 mice for 18 to 25 days. Single, 7-milligram fragments (prepared from one of the several excised passaged tumors) were implanted subcutaneously into BDF$_1$ mice. Animals were treated with drug intraperitoneally on Days 2 and 9, or 2, 9, and 16 following tumor implantation. On Day 20, individual tumor weights were calculated from two dimensional measurements employing the formula: tumor weight $(mg)=(L\times W^2)/2$. The median tumor weight for each animal group (10 mice per drug dose) was derived by ranking the tumor weights (including cures) and recording the midpoint between the fifth and sixth tumor weights. The criterion for activity in this test was a % T/C equal to or less than 42% which was considered indicative of activity, and a reproducible % T/C equal to or less than 10% for an indication of substantive activity. In this instance, the tumor weight % T/C values represent the ratio of tumor weights of treated to untreated test animals, expressed as a percentage. The deterination of percent tumor weight inhibition brought about by the drug was determined by subtracting from 100%. For example, a tumor weight % T/C of 42% corresponds to a Tumor Weight Inhibition (TWI) of 58%.

Mouse Mammary Tumor Was propagated in CD8F$_1$ female mice as spontaneous tumors. Approximately 10$^6$ cells were then implanted subcutaneously into CD8F$_1$ mice. Animals were treated with drug ip on days 1, 8, 15, 22, and 29 following tumor implantation. At the end of the experiment (30 days), individual tumor weights were determined by caliper measurements. Each tumor weight was calculated as described previously for colon 26 and 38 tumors. A criterion of % T/C tumor weight of 42% or less was considered indicative of activity, with a reproducible 10% T/C tumor weight or less indicative of substantive activity.

(b) Controls.

In all of the mouse tumor studies described above, routine controls consisted of matching ten normal mice (with no tumors) to each tumor-bearing treatment group and injecting them with the same drug at the same dosages, schedules, days of administration, and drug route as the tumor-bearing mice. In this way, drug-induced toxicity (lethality and weight loss) could be clearly separated from the effects of the drug on the tumors. The results of these tests appear in Table IV.

TABLE IV

Antitumor Activity of Trimetrexate Against a Spectrum of Murine Tumors

| Mouse Tumor System (Treatment Schedule) | Trimetrexate Dose Range (mg/kg) | Optimal Dose (mg/kg) | Life Span % T/C | Life Span % ILS | Tumor Weight Inhibition % TWI |
|---|---|---|---|---|---|
| B-16 Melanoma | 40–1.25 | 20 | 164% | 64% | |
| (Ip daily, Days 1–9) | 20–0.62 | 20 | 150% | 50% | |
| L1210 | 80–5 | 80 | 196% | 96% | |
| (Ip daily, Days 1–9) | 80–5 | 20 | 172% | 72% | |
| P388 | 80–2.5 | 40 | 243% | 143% | |
| (Ip daily, Days 1–9) | 80–2.5 | 40 | 242% | 142% | |
| Colon 26 | 120–3.75 | 60 | 215% | 115% | |
| (Ip every 4 days, Days 1–5) | 120–3.75 | 30 | 156% | 56% | |
| Lewis lung carcinoma (IV daily, Days 1–9) | 40–1.25 | 40 | Negligible | | |
| Colon 38 | 120–3.75 | 120 | | | 96% |
| (Sc every 7 days, Days 2–9) | 60–1.88 | 60 | | | 85% |
| CD8F$_1$ Mammary tumor | 270–35 | 180 | | | 100% |
| (Sc every 7 days, Days 1,8,15,22,19) | 120–3.75 | 120 | | | 100% |

The data in Table IV show that trimetrexate exhibits good activity against intraperitoneally implanted B-16 melanoma, colon adenocarcinomas 26 and 38, L1210 and P388 leukemias, and subcutaneously implanted CD8F$_1$ mammary tumors.

The dose schedule dependence of trimetrexate was tested against transplanted P388 leukemia using the protocol outlined above. The data from those tests appear in Table V.

TABLE V

Schedule Dependence of Trimetrexate Against P388 Murine Leukemia

| Dose (mg/kg) | Schedule | Weight Change (Grams) | % T/C |
|---|---|---|---|
| 180 | Day 1 only | | 12 |
| 120 | | | 113 |
| 80 | | | 104 |
| 53 | | | 100 |
| 180 | Days 1, 5, and 9 | | 9 |
| 120 | | −2.5 | 154 |
| 80 | | 1.3 | 119 |
| 53 | | 2.9 | 116 |
| 75 | Days 1 and 9 | −2.6 | 181 |
| 50 | | 0.3 | 166 |
| 33 | | 0.8 | 169 |
| 22 | | 1.8 | 164 |
| 45 | Every 3 hours, daily | −1.7 | 212 |
| 30 | Days 1, 5, and 9 | 0.6 | 203 |
| 20 | | −0.2 | 194 |
| 13 | | 1.0 | 185 |

The data in Table V illustrate that in tests of trimetrexate against P388 murine leukemia, in terms of minimal test animal weight loss and maximum life span response, the optimal dose regimen for the evaluation of trimetrexate was about 30 mg/kg/injection every three hours on Days 1, 5, and 9. This regimen was adopted as optimal for further studies evaluating the effectiveness of trimetrexate against transplanted P388 murine leukemia.

Preclinical Studies of Combination Therapy Employing Trimetrexate

Several studies were carried out to determine the potential for therapeutic synergy of trimetrexate with several clinically active anticancer agents. In these studies, the tumor model selected was P388 murine leukemia because of its demonstrated high predictability for clinical efficacy against a broad spectrum of human tumors. (See, for example, Vendetti, "Relevance of Transplantable Animal-Tumor Systems to the Selection of New Agents for Clinical Trial," *Pharmacological Basis of Cancer Chemotherapy*. Williams and Wilkins, Baltimore, 1975, and Simpson Herren, et al., "Evaluation of In Vivo Tumor Models for Predicting Clinical Activity for Anticancer Drugs," *Proc. Am. Assoc. Cancer Res.*, 26: 330 (1985).

In these studies, two drugs were determined to possess therapeutic synergy if a combination dose regimen of the two drugs produced a significantly better tumor cell kill than either of the single agents at optimal or maximum tolerated doses. The "degree of synergy" was defined as net logs of tumor cell kill by the optimum combination regimen minus net logs of tumor cell kill by the optimal dose of the most active single agent. Differences in cell kill of greater than ten-fold (one log) were considered indicative of therapeutic synergy. Observed therapeutic synergy values ranged from about 100-fold to an upper value of greater than 10,000-fold.

CD2F$_1$ mice were quarantined for at least two weeks prior to allocation to test groups. P388 leukemia was passaged in DBA2 mice according to standard protocols of the National Cancer Institute. On Day 0 of a given test, all mice in the test were randomized, injected intraperitoneally with suitably diluted ascites fluid from P388 tumor-bearing donor mice and rerandomized to test cages.

The initial inoculum for all but titration groups was $10^6$ cells as determined by hemocytometer count. Each experiment contained an internal control and tumor titration which enabled the determination of the tumor doubling time and estimates of the log cell kill and number of tumor cells surviving treatment.

Drug treatment was begun either on Day 1 or on Day 4 depending upon the relative activity of the agents being tested. The treatment regimens employed were those determined to be optimal for each drug, and are given in Table VI.

TABLE VI

| Drug | Route of Administration (Diluent) | Regimen |
|---|---|---|
| Trimetrexate | ip (Water) | Administered every 3 hours, Days 1, 5, and 9, or Days 4, 8, and 12 |
| Methotrexate | ip (2% NaHCO$_3$) | Administered once daily, Days 4–12 |
| 6-Thioguanine | ip (Saline + base) | Administered once daily, Days 1–9 |

Treatment Regimens Employed in Combination Therapy Studies

TABLE VI-continued

| Drug | Route of Administration (Diluent) | Regimen |
|---|---|---|
| 5-Fluorouracil | ip (Saline) | Administered daily, Days 1–9 |
| Cyclophosphamide | ip (Saline) | Administered once daily, Days 4, 8, and 12 |
| Vincristine | iv (Saline) | Administered once daily, Days 1, 5, and 9 |
| Doxorubicin | iv (Saline) | Administered once daily, Days 1, 5, and 9 |
| Cisplatin | ip (Saline) | Administered once daily, Days 4, 8, and 12 |

Treatment Regimens Employed in Combination Therapy Studies

All of the drugs were injected within one hour of dissolution, with the exception of trimetrexate which was made up fresh twice daily. All mice were treated on the basis of average cage-group weight.

In drug combination regimens, trimetrexate was given approximately 30 minutes before the other therapeutic agents when the route of administration of the other agent was ip. When the second agent was administered by the iv route, trimetrexate was administered within one minute. On days when trimetrexate was administered to the test animals, the other antitumor agent was administered together with the first trimetrexate dose of the day.

Group average weights were determined for all groups on Days 1, 5, and 9 for "early stage" P388 tests and on Days 4, 8, and 12 for "advanced stage" P388 tests. Animals were monitored for life span. Calculations of median day of death, percentage increase in life span (% ILS), number of tumor cells surviving treatment, and net logs of tumor cell kill employed standard methodology.

Tumor-free survivors were excluded from these calculations. Thus, the end-points reflect the effect of therapy upon treatment failures.

Studies of combination therapy of trimetrexate with doxorubicin, 5-fluorouracil, vincristine, and 6-thioguanine were carried out against early stage P388 leukemia (i.e. $4 \times 10^6$ to $5 \times 10^6$ tumor cells present at first treatment), while studies of combination therapy of trimetrexate with methotrexate, cyclophosphamide and cisplatin were carried out against P388 leukemia in a more advanced stage (i.e. about $1 \times 10^8$ tumor cells present at first treatment). This was done to avoid curative therapy by methotrexate, cyclophosphamide, or cisplatin as single agents which would preclude the determination of and therapeutic synergy.

A summary of the results of these therapeutic synergy tests appears in Table VII.

TABLE VII

Combination Chemotherapy Studies
Degree of Observed Therapeutic Synergy
Against P388 Murine Leukemia

| Drug Combination | Early Stage P388 Leukemia | | |
|---|---|---|---|
| | Degree of Synergy | | |
| | Test 1 | Test 2 | Mean |
| Trimetrexate + doxorubicin | 0.7 | 3.1–5.6 | 2.1–33.2 |
| Trimetrexate + | 2.1 | 1.3 | 1.7 |

TABLE VII-continued

Combination Chemotherapy Studies
Degree of Observed Therapeutic Synergy
Against P388 Murine Leukemia

| | | | |
|---|---|---|---|
| 5-fluorouracil | | | |
| Trimetrexate + vincristine | 2.1 | 1.6 | 1.8 |
| Trimetrexate + 6-thioguanine | 2.5 | 3.8 | 3.2 |
| Advanced Stage P388 Leukemia | | | |
| Trimetrexate + methotrexate | Toxic | 1.4 | NA |
| Trimetrexate + cyclophosphamide | 6.1 | >3.1 | >4.6 |
| Trimetrexate + cisplatin | 0.5 | 2.7 | 1.6 |

Trimetrexate + Doxorubicin

In Test 1, the combination of trimetrexate with doxorubicin on four different dose regimens (31 and 4, 31 and 2.7, 20 and 4, and 20 and 2.7 mg/kg/injection, respectively) produced approximately 0.7 logs better net tumor cell kill than the best results by either agent administered individually. Doxorubicin as a single agent was somewhat less active than expected based upon historical data, but the test was technically satisfactory.

In Test 2, all six of the combination regimens produced better tumor cell kill than either of the single agents. The optimal combination regimen (trimetrexate at 46 mg/kg/injection and doxorubicin at 6 mg/kg/injection) produced 5.6 logs greater tumor cell kill than the best result of the agents administered singly.

These studies indicate that the combination of trimetrexate and doxorubicin is therapeutically synergystic, producing an average of three logs better net tumor cell kill than optimal doses of either of the agents when administered individually.

Trimetrexate + 5-Fluorouracil

In Test 1, several of the combination regimens were superior to either of the two single agents, with two of the combination regimens reducing the calculated tumor cell burden in the host animal to a single cell. Thus, the optimal regimens produced 2.1 logs greater tumor cell kill than the most active of the single agents.

Test 2 confirmed these results with several of the combination regimens yielding net tumor cell kills 1.3 logs greater than 5-fluorouracil alone, with an average degree of therapeutic synergy for the tests of 1.7 logs improved tumor cell kill.

Trimetrexate + Vincristine

In Test 1, all five of the tolerated combination regimens produced better reductions in the tumor burden in the host animals than did trimetrexate, which was the more active of the two single agents. The most active of the combination regimens reduced the estimated tumor burden to just 150 cells, a 2.1 log better cell kill than that obtained by treatment with trimetrexate alone. Similar results were obtained in Test 2 where vincristine was the more active of the single agents. The average degree of synergy observed for this combination therapy was 1.8 logs improved tumor cell kill.

Trimetrexate + 6-Thioguanine

Marked therapeutic synergy was observed with trimetrexate administered in combination with 6-thioguanine in both tests. In Test 1, the optimal combination regimen reduced the estimated tumor burden in the host animal to 70 cells. The net tumor cell kill was 2.5 logs better than that obtained with trimetrexate alone at its optimal dose. Additionally, the best combination regimen in that test was with the lowest doses tested.

In Test 2, dose levels for the combination regimen were lowered while dose levels for the single agents were kept the same as in Test 1. The optimal combination regimen once again reduced the estimated tumor burden in the host animal to about 70 cells, a 3.8 log better tumor cell kill than obtained by administration of the agents individually. The average degree of synergy obtained in the two tests was 3.2 logs net tumor cell kill.

Trimetrexate + Cyclophosphamide

Combination therapy with trimetrexate and cyclophosphamide was highly therapeutically synergistic in both tests performed. In Test 1, three of the six combination regimens reduced the estimated tumor burden in the host animal to 10 cells or less. The optimal combination produced more than six logs better cell kill than with cyclophosphamide alone. In Test 2, the optimal regimen cured nine out of ten of the ten treated mice, and two of the other treatment regimens reduced the estimated tumor burden to less than 20 cells.

Trimetrexate + Cisplatin

Test 1 indicated that the combination of these agents did not produce significantly better cell kill at tolerated doses than did administration of the single agents alone. The best of the combination regimens produced only 0.5 log units better tumor cell kill than the individual agents. However, in Test 2, cisplatin was considerably less active as a single agent, and the optimal regimen produced 2.7 logs better tumor cell kill, with an average degree of therapeutic synergy for the two tests of 1.6 log units. Thus, the tests indicate marginal synergy in the combination.

Trimetrexate + Methotrexate

In Test 1, the combination of trimetrexate and methotrexate appeared to be synergistic with respect to host animal toxicity at the dose levels employed. In Test 2, the dose levels were reduced, and a slight degree of therapeutic synergy (1.4 log units improved tumor cell kill) was observed for the combination. These results indicate some benefit accrues to the use of the combination of the two drugs, although they must be employed at lower doses.

Clinical Trials with Trimetrexate

Phase I Trials

Several Phase I clinical trials employing trimetrexate in human patients were carried out. In one study, 36 patients were treated with trimetrexate as a single agent at daily doses of 0.5 mg/m$^2$/day to 12 mg/m$^2$/day administered intravenously for five days.

In additional Phase I clinical studies, patients were administered trimetrexate with single intravenous doses ranging between 5 and 450 mg/m$^2$ and with weekly doses of slightly greater than 100 mg/m$^2$.

Of the patients administered trimetrexate as a single agent, favorable responses were observed in two patients having non-small cell lung cancer, four patients having colon carcinoma, two patients with head and neck (squamous) cancers, one patient with cancer of the pancreas, and two patients with salivary gland cancer.

The favorable response in patients having non-small lung cancer was surprising in light of both the fact that this type of cancer is generally considered refractory to most chemotherapeutic agents.

Phase II Trials

Non-Small Cell Lung Cancer

The efficacy and safety of trimetrexate in the treatment of patients with non-small cell lung cancer was evaluated in a 16-center Phase II study. Seventy patients participated in the multicenter study, with a group of 59 patients considered evaluable.

The histologies represented by the patients included adenocarcinoma (24 patients), squamous cell (17 patients), and large cell (10 patients).

Initially, all patients received a single 8 mg/m$^2$ dose of trimetrexate daily for five days of a 21-day treatment course. The dose was administered at three- or four-week intervals, with the number of treatment courses dependent upon the patient's response.

The number of treatment courses administered to each patient with non-small cell lung cancer ranged from 1 to 12, with a median of 2 courses. The median dose increased from 8 mg/m$^2$ for course 1 to 38.18 mg/m$^2$ for course 12. There was a wide patient variation in dosing, with a range of from 5.62 to 38.18 mg/m$^2$/day×5 over all courses. No patient received daily doses of trimetrexate greater than the dose which corresponded to their actual body surface area. A total of 234 courses of trimetrexate were administered to the 70 patients in the study.

Objective response was determined by a decrease from baseline in tumor size as set forth by the World Health Organization (WHO) response criteria. Duration of response was measured from the date of first treatment to the first date when progressive disease was documented.

Fifty-nine of the originally enrolled 70 patients were evaluated. Responses were classified as complete or partial. A complete response was defined as no evidence of disease and a partial response as a 50% or greater decrease in overall tumor size without evidence of progression in 28 days.

Eleven patients (19%; 95% confidence interval 9%–29%) achieved a partial response with a median duration of 15.3 weeks (range 5.6–40.7). One additional patient achieved a 50% regression only by liver measurements.

For those patients who responded to treatment with trimetrexate, the median time to progressive disease was 24.9 weeks (range 11.1–47.0). Progressive disease was defined as a 25% increase in either overall size of the lesions or in any single lesion or the appearance of a new lesion. For the 25 patients (42%) who only experienced progressive disease, the median time to progression was 3.4 weeks. For the 23 patients (39%) with stable disease, the median time to progressive disease was 15.7 weeks. The median time to progressive disease for 55 of the 59 evaluable patients was 7.9 weeks (range 1.9–75.0). Four patients had not experienced progressive disease at the end of the reporting period for the Phase II study.

In this multicenter Phase II study, trimetrexate achieved a 19% response rate in non-small cell lung cancer with an overall median survival time of 26.4 weeks. This response rate compares favorably with the response rates for all other single agent chemotherapy agents which have been used to treat non-small lung cell cancer in human patients.

Head and Neck Cancer

The efficacy and safety of trimetrexate in the treatment of patients with metastatic squamous cell cancer of the head and neck was evaluated in an 11-center Phase II study. Forty-three patients participated in the multicenter study, with a group of 38 patients considered evaluable.

The primary sites of disease in the patients included head and neck (not otherwise specified), hypopharynx, floor of the mouth, oropharynx, tongue, and other parts of the mouth, nasal cavity, and larynx.

Patients were initially treated intravenously with 8 mg/m$^2$/day of trimetrexate on Days 1 through 5 of a 21-day treatment cycle. Patients were evaluated after each treatment course and were withdrawn from the study if progressive disease was documented. Patients were eligible to received six courses of treatment if stable disease was documented, or were eligible to receive continued treatment with trimetrexate if a response was documented. The dose of trimetrexate was adjusted for each patient prior to each subsequent course of treatment based upon the patient reaction to the drug in the preceding course of treatment, and ranged from 8 mg/m$^2$/day to about 20 mg/m$^2$/day.

The number of courses of treatment administered to each patient with head and neck cancer ranged from 1 to 14, with a median of 2 courses. A total of 136 courses of treatment were administered to the 43 patients during the study.

Ten (26%; 95% confidence interval 12–40%) of the evaluable patients in the study were determined to have achieved a partial response to treatment with trimetrexate. These ten patients had a median duration of response of 12.2 weeks (range 4.1–59+ weeks). The median time to progressive disease was 19.1 weeks (range 9.3–74+ weeks). Nineteen of the patients achieved stable disease.

Breast Cancer

The efficacy and safety of trimetrexate in the treatment of patients with breast cancer was evaluated in an 10-center Phase II study. Twenty-eight patients participated in the multicenter study, with a group of 20 patients considered evaluable. These patients were nonresponsive to and/or had demonstrated progressive disease after conventional surgery or radiotherapy. All patients had metastatic disease and the principal sites of metastasis included lung, bone, and liver.

Patients were initially treated intravenously with 8 mg/m$^2$/day of trimetrexate on Days 1 through 5 of a 21-day treatment cycle. Patients were evaluated after each treatment course and were withdrawn from the study if progressive disease was documented. Patients were eligible to received six courses of treatment if stable disease was documented; treatment beyond six courses was left to the discretion of the physician. The dose of trimetrexate was adjusted for each patient prior to each subsequent course of treatment based upon the patient reaction to the drug in the preceding course of treatment, and ranged from 8 mg/m$^2$/day to about 20 gm/m$^2$/day. A total of 91 courses of treatment were administered to the patients in the study.

Of the 20 evaluable patients, 3 (15%; p5% confidence interval 0–30.6%) achieved a partial response with a median duration of 13.1 weeks (range 6.4–18.7+ weeks), and 10 patients remained with stable disease.

Administration of Trimetrexate in Single Agent Therapy

When used alone, trimetrexate may be administered by intermittent intravenous injection at doses of 50–500 mg/m$^2$; by repeated intravenous injection at doses of 2–20 mg/m$^2$/day; or by continuous intravenous or arterial infusion at doses of 2–20 mg/m$^2$/day. Data indicate that trimetrexate is about 80% bioavailable when administered orally. The drug may thus also be orally administered in regimens similar to those above. In retreatment regimens, the dose is adjusted to reflect patient tolerance of the prior treatment.

Because of the increased solubility of salts of trimetrexate over the free base form, the salts are preferred for administration. The preferred salt for parenteral administration is the D-glucuronate salt, while the monosiethionate (i.e. the 2-hydroxyethanesulfonate) salt is preferred for oral administration. The preparation of these salts of trimetrexate and of pharmaceutical compositions containing these salts is described in U.S. Pat. No. 4,376,858 which is incorporated herein by reference.

Administration of Trimetrexate in Combination Therapy with Other Antineoplastic Agents Trimetrexate may also be coadministered in combination with other clinically-proven antineoplastic agents. When employed in combination with one of these agents, the dosages of trimetrexate and the additional agent are adjusted downward from levels employed when each agent is used singly, to reflect the combined efficacy of the two drugs. The determination of the exact dosages for a given patient varies, dependent upon a number of factors including the drug combination employed, the particular disease being treated, and the condition and prior history of the patient, but is within the skill of the art.

Specific dose regimens for other known and approved antineoplastic agents are given, for example, in the product descriptions found in the *Physician's Desk Reference,* 39th Edition, Medical Economics Company, Inc., Oradell, N.J., 1985. Illustrative of dosages regimens for these drugs are the following:

Doxorubicin: 60–75 mg/m$^2$ as a single intravenous injection administered at 21-day intervals; weekly intravenous injection at doses of 20 mg/m$^2$; or 30 mg/m$^2$ doses on each of three successive days repeated every four weeks.

Cyclophosphamide: for induction therapy, 1500–1800 mg/m$^2$ administered intravenously in divided doses over a period of three to five days; for maintenance therapy, 350–550 mg/m$^2$ administered every 7–10 days or 110–185 mg/m$^2$ administered intravenously twice weekly.

5-Fluorouracil: Initial therapy—Doses of 12 mg/m$^2$ are given intravenously once daily for 4 successive days with the daily dose not exceeding 800 mg. If no toxicity is observed at any time during the course of the therapy, 6 mg/kg are given intravenously on the 6th, 8th, 10th, and 12th days. No therapy is given on the 5th, 7th, 9th, or 11th days. In poor risk patients or those who are not in an adequate nutritional state, a daily dose of 6 mg/kg for three days, with the daily dose not exceeding 400 mg. If no toxicity is observed at any time during the treatment, 3 mg/kg may be given on the 5th, 7th, and 9th days. No therapy is given on the 4th, 6th, or 8th days. A sequence of injections on either schedule constitutes a course of therapy.

Maintenance therapy—Repeat the dosage regimen of the first course of therapy, beginning thirty days after the last day of the previous course of treatment. Administer a maintenance dose of 10 to 15 mg/kg/week. Total doses should not exceed 1 gram, and reduced doses should be used in poor risk patients.

6-Thioguanine: Orally administered doses of about 2 mg/kg of body weight per day. The total daily dose may be given at one time. If after four weeks of dosage at this level there is no improvement, the dosage may be cautiously increased to 3 mg/kg/day.

Vincristine: Weekly intravenous doses of 2 mg/m$^2$ for children and 1.4 mg/m$^2$ for adults.

Methotrexate: For choriocarcinoma, intramuscular injections of doses of 15 to 30 mg daily for a five-day course, such courses repeated as needed with rest period of one or more weeks interposed between courses of therapy. For leukemias, twice weekly intramuscular injections in doses of 30 mg/m$^2$. For mycosis fungoides, weekly intramuscular injections of doses of 50 mg or, alternatively, of 25 mg twice weekly.

Cisplatin: For advanced bladder cancer, intravenous injections of doses of 50–70 mg/m$^2$ once every three to four weeks.

We claim:

1. A method of treating non-small cell lung cancer, head and neck cancers, or breast cancer in a mammal in need thereof comprising administering to said mammal an antineoplastically effective amount of 5-methyl-6-[[(3,4,5-trimethoxyphenyl)amino]-methyl]-2,4-quinazolinediamine or a pharmaceutically acceptable salt thereof alone or in combination with an antineoplastically effective amount of a compound selected from the group consisting of
   (a) (8S,10S)-10-[(3-amino-2,3,6-trideoxy-α-L-lyxo-hexopyranosyl)oxy]-8-glycoloyl-7,8,9,10-tetrahydro-6,8,11-trihydroxy-1-methoxy-5,12-naphthacenedione or a pharmaceutically acceptable salt thereof;
   (b) 5-fluoro-2,4(1H,3H)-pyrimidinedione or a pharmaceutically acceptable salt thereof;
   (c) 2-amino-1,7-dihydro-6H-purine-6-thione or a pharmaceutically acceptable salt thereof;
   (d) 22-oxo-vincaleukoblastine or a pharmaceutically acceptable salt thereof;
   (e) 2-bis[(2-chloroethyl)amino]tetrahydro-2H-1,3,2- oxazaphosphorine, 2-oxide, or a pharmaceutically acceptable salt thereof;
   (f) N-[4-[[(2,4-diamino-6-pteridinyl)methyl]methylamino]benzoyl]-L-glutamic acid, or a pharmaceutically acceptable salt thereof; or
   (g) cis-diamminedichloroplatinum (II).

2. The method of claim 1 wherein said pharmaceutically acceptale salt is the D-glucuronate salt.

3. The method of claim 1 wherein said pharmaceutically acceptable salt is the 2-hydroxyethanesulfonate salt.

4. A method of treating non-small cell lung cancer in a mammal in need thereof comprising administering to said mammal an antineoplastically effective amount of 5-methyl-6-[[(3,4,5 trimethoxyphenyl)amino]methyl]-2,4-quinazolinediamine or a pharmaceutically acceptable salt thereof.

5. The method as defined in claim 4 wherein said 5-methyl-6-[[(3,4,5-trimethoxyphenyl)amino]methyl]-2,4-quinazolinediamine or a pharmaceutically acceptable salt thereof is administered at a dose of between about 5.6 mg/m$^2$ and about 38.18 mg/m$^2$.

6. A method of treating head and neck cancers in a mammal in need thereof comprising administering to said mammal an antineoplastically effective amount of 5-methyl-6-[[(3,4,5-trimethoxyphenyl)amino]methyl]-2,4-quinazolinediamine or a pharmaceutically acceptable salt thereof.

7. The method as defined in claim 6 wherein said 5-methyl-6-[[(3,4,5-trimethoxyphenyl)amino]methyl]-2,4-quinazolinediamine or a pharmaceutically acceptable salt thereof is administered at a dose of between about 8 mg/m$^2$ and about 20 mg/m$^2$.

8. A method of treating breast cancer in a mammal in need thereof comprising administering to said mammal an antineoplastically effective amount of 5-methyl-6-[[(3,4,5-trimethoxyphenyl)amino]methyl]-2,4-quinazolinediamine or a pharmaceutically acceptable salt thereof.

9. The method as defined in claim 8 wherein said 5-methyl-6-[[(3,4,5-trimethoxyphenyl)amino]methyl]-2,4-quinazolinediamine or a pharmaceutically acceptable salt thereof is administered at a dose of between about 8 mg/m$^2$ and about 20 mg/m$^2$.

10. A method of treating non-small cell lung cancer, head and neck cancers, or breast cancer in a mammal in need thereof comprising administering to said mammal an antineoplastically effective amount of 5-methyl-6-[(3,4,5-trimethoxyphenyl)amino]methyl]-2,4-quinazolinediamine or a pharmaceutically acceptable salt thereof alone or in combination with an antineoplastically effective amount of (8S,10S)-10-[(3-amino-2,3,6-trideoxy-α-L-lyxo-hexopyranosyl)oxy]-8-glycoloyl-7,8,9,10-tetrahydro-6,8,11-trihydroxy-1-methoxy-5,12-naphthacenedione or a pharmaceutically acceptable salt thereof.

11. A method of treating non-small cell lung cancer, head and neck cancers, or breast cancer in a mammal in need thereof comprising administering to said mammal an antineoplastically effective amount of 5-methyl-6-[[(3,4,5-trimethoxyphenyl)amino]methyl]-2,4-quinazolinediamine or a pharmaceutically acceptable salt thereof alone or in combination with an antineoplastically effective amount of 5-fluoro-2,4(1H,3H)-pyrimidinedione or a pharmaceutically acceptable salt thereof.

12. A method of treating non-small cell lung cancer, head and neck cancers, or breast cancer in a mammal in need thereof comprising administering to said mammal an antineoplastically effective amount of 5-methyl-6-[[(3,4,5-trimethoxyphenyl)amino]methyl]-2,4-quinazolinediamine or a pharmaceutically acceptable salt thereof alone or in combination with an antineoplastically effective amount of 2-amino-1,7-dihydro-6H-purine-6-thione or a pharmaceutically acceptable salt thereof.

13. A method of treating non-small cell lung cancer, head and neck cancers, or breast cancer in a mammal in need thereof comprising administering to said mammal an antineoplastically effective amount of 5-methyl-6-[[(3,4,5-trimethoxyphenyl)amino]methyl]-2,4-quinazolinediamine or a pharmaceutically acceptable salt thereof alone or in combination with an antineoplastically effective amount of 22-oxo-vincaleukoblastine or a pharmaceutically acceptable salt thereof.

14. A method of treating non-small cell lung cancer, head and neck cancers, or breast cancer in a mammal in need thereof comprising administering to said mammal an antineoplastically effective amount of 5-methyl-6-[[(3,4,5-trimethoxyphenyl)amino]methyl-2,4-quinazolinediamine or a pharmaceutically acceptable salt thereof alone or in combination with an antineoplastically effective amount of 2-bis[(2-chloroethyl)amino]-tetrahydro-2H-1,3,2-oxazaphosphorine, 2-oxide, or a pharmaceutically acceptable salt thereof.

15. A method of treating non-small cell lung cancer, head and neck cancers, or breast cancer in a mammal in need thereof comprising administering to said mammal an antineoplastically effective amount of 5-methyl-6-[[(3,4,5-trimethoxyphenyl)amino]methyl]-2,4-quinazolinediamine or a pharmaceutically acceptable salt thereof alone or in combination with an antineoplastically effective amount of N-[4-[[(2,4-diamino-6-pteridinyl)methyl]methylamino]benzoyl]-L-glutamic acid, or a pharmaceutically acceptable salt thereof.

16. A method of treating non-small cell lung cancer, head and neck cancers, or breast cancer in a mammal in need thereof comprising administering to said mammal an antineoplastically effective amount of 5-methyl-6-[[(3,4,5-trimethoxyphenyl)amino]methyl]-2,4-quinazolinediamine or a pharmaceutically acceptable salt thereof alone or in combination with an antineoplastically effective amount of cis-diamminedichloroplatinum (II).

* * * * *